(12) United States Patent
Zutter

(10) Patent No.: US 7,956,201 B2
(45) Date of Patent: Jun. 7, 2011

(54) PROCESS FOR THE PREPARATION OF (S)-4-FLUOROMETHYL-DIHYDRO-FURAN-2-ONE

(75) Inventor: Ulrich Zutter, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 845 days.

(21) Appl. No.: 11/873,072

(22) Filed: Oct. 16, 2007

(65) Prior Publication Data

US 2008/0108816 A1    May 8, 2008

(30) Foreign Application Priority Data

Nov. 6, 2006  (EP) .................................... 06123512

(51) Int. Cl.
*C07D 455/06* (2006.01)
*C07D 307/20* (2006.01)
(52) U.S. Cl. ........................... 549/324; 549/326; 546/95
(58) Field of Classification Search .................. 549/324, 549/326; 546/95
See application file for complete search history.

(56) References Cited

U.S. PATENT DOCUMENTS 5,629,432 A * 5/1997 Shepherd ...................... 549/326

FOREIGN PATENT DOCUMENTS

WO  WO 2005/000848  1/2005
WO  WO 2006/125728  11/2006

OTHER PUBLICATIONS

Hughes, G. et al, *Jour. Am. Chem. Soc.* (2003) 125, 11253-11258.

* cited by examiner

*Primary Examiner* — Rita J Desai
*Assistant Examiner* — David K O'Dell
(74) *Attorney, Agent, or Firm* — George W. Johnston; Dennis P. Tramaloni; Samuel H. Megerditchian

(57) ABSTRACT

The present invention relates to a process of the preparation of (S)-4-fluoromethyl-dihydro-furan-2-one of the formula

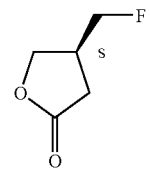

by employing a dialkylmalonate of the formula

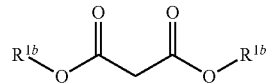

wherein $R^{1b}$ is lower alkyl, and the use of this process for the manufacture of DPP-IV inhibitors that are useful for the treatment and/or prophylaxis of diseases such as diabetes.

16 Claims, No Drawings

PROCESS FOR THE PREPARATION OF (S)-4-FLUOROMETHYL-DIHYDRO-FURAN-2-ONE

PRIORITY TO RELATED APPLICATION(S)

This application claims the benefit of European Patent Application No. 06123512.3, filed Nov. 6, 2006, which is hereby incorporated by reference in its entirety.

FIELD OF THE INVENTION

The present invention relates to a process of the preparation of (S)-4-fluoromethyl-dihydro-furan-2-one of the formula

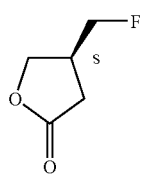

I and the use of this process for the manufacture of pyrido[2,1-a]isoquinoline derivatives of the formula

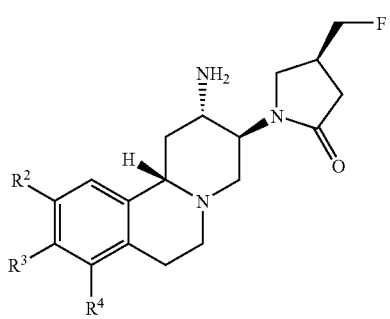

II which are useful for the treatment and/or prophylaxis of diseases which are associated with DPP IV.

All document cited or relied upon below are expressly incorporated herein by reference.

BACKGROUND OF THE INVENTION

The pyrido[2,1-a]isoquinoline derivatives of formula II

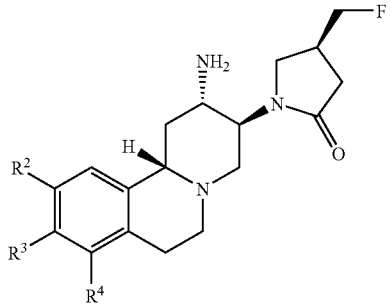

II wherein
$R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group consisting of lower alkoxycarbonyl, aryl and heterocyclyl, and the pharmaceutically acceptable salts thereof are disclosed in PCT International Patent Appl. WO 2005/000848.

SUMMARY OF THE INVENTION

In an embodiment of the present invention, provided is a process for the preparation of (S)-4-fluoromethyl-dihydro-furan-2-one of the formula

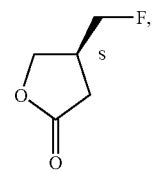

I comprising the steps:
a) conversion of a glycidyl ether of the formula

III wherein $R^{1a}$ is a protecting group, with a fluoride salt to provide a fluoro hydrin of formula

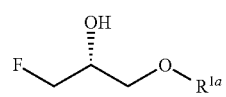

IV wherein $R^{1a}$ is as defined above;
b) esterification of the hydroxy group in the fluoro hydrin of the formula IV with a sulfonic acid derivative;
c) ester substitution with a dialkylmalonate of the formula

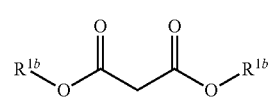

V wherein $R^{1b}$ is lower alkyl or lower phenylalkyl, in the presence of a base to provide an intermediate of the formula

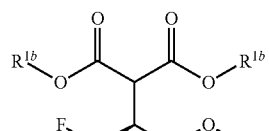

VI wherein $R^{1a}$ and $R^{1b}$ are as defined above, followed by
d) cyclization, hydrolysis and decarboxylation under acidic conditions.

In another embodiment of the present invention, provided is a compound of formula

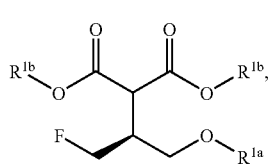

VI wherein $R^{1a}$ is a protecting group and $R^{1b}$ is lower alkyl or lower phenylalkyl.

In a further embodiment of the present invention, provided is a process for the preparation of pyrido[2,1-a]isoquinoline derivatives of the formula

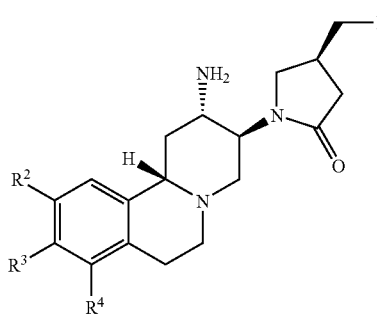

II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, comprising the process according to claims 1 to 14 followed by e) coupling of the (S)-4-fluoromethyl-dihydro-furan-2-one of formula

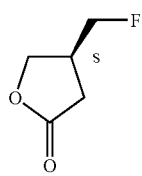

I with an amino-pyrido[2,1-a]isoquinoline derivative of formula

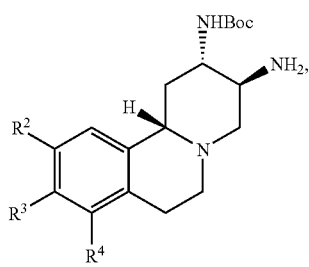

VIII wherein $R^2$, $R^3$ and $R^4$ are as defined above, f) cyclization of the obtained amide of formula

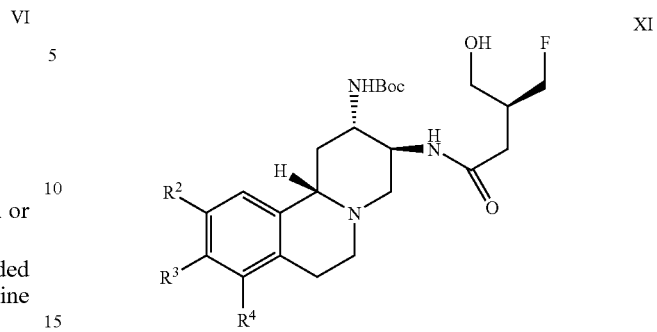

XI wherein $R^2$, $R^3$ and $R^4$ are as defined above,
in the presence of a base to obtain a compound of formula

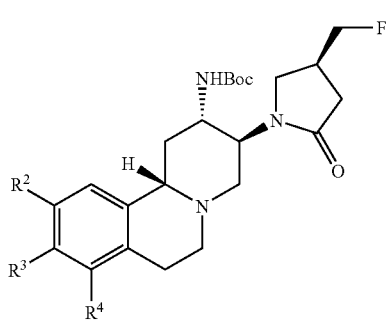

IX wherein $R^2$, $R^3$ and $R^4$ are as defined above and
g) deprotection of the amino group.

DETAILED DESCRIPTION

The invention provides for intermediates in the manufacture of the pyrido[2,1-a]isoquinoline derivatives of formula II, namely the (S)-4-fluoromethyl-dihydro-furan-2-one of the formula I.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "lower phenylalkyl" refers to lower alkyl groups as defined above wherein at least one of the hydrogen atoms of the lower alkyl group is replaced by a phenyl group. The phenyl ring may be substituted as defined herein. Examples of preferred lower phenylalkyl groups are benzyl, 4-methylbenzyl, 4-fluorobenzyl, 3-methoxybenzyl, 4-methoxybenzyl, 2-phenylethyl and 3-phenylpropyl. Especially preferred is benzyl.

The term "lower alkenyl" as used herein denotes an unsubstituted or substituted hydrocarbon chain radical having from 2 to 6 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkoxy" refers to the group R'—O—, wherein R' is alkyl. The term "lower-alkoxy" refers to the group R'—O—, wherein R' is a lower alkyl group as defined above. Examples of lower alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is a lower alkyl group as defined above.

The term "aryl" refers to an aromatic monovalent mono- or polycarbocyclic radical, such as phenyl or naphthyl, preferably phenyl, which may optionally be mono-, di- or tri-substituted, independently, by lower alkyl, lower alkoxy, halo, cyano, azido, amino, di-lower alkyl amino or hydroxy.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl and cyclobutyl being preferred. Such cycloalkyl residues may optionally be mono-, di- or tri-substituted, independently, by lower alkyl or by halogen.

The term "heterocyclyl" refers to a 5- or 6-membered aromatic or saturated N-heterocyclic residue, which may optionally contain a further nitrogen or oxygen atom, such as imidazolyl, pyrazolyl, thiazolyl, pyridyl, pyrimidyl, morpholino, piperazino, piperidino or pyrrolidino, preferably pyridyl, thiazolyl or morpholino. Such heterocyclic rings may optionally be mono-, di- or tri-substituted, independently, by lower alkyl, lower alkoxy, halo, cyano, azido, amino, di-lower alkyl amino or hydroxy. Preferable substituent is lower alkyl, with methyl being preferred.

The term "pharmaceutically acceptable salts" embraces salts of the compounds of formula II with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In detail, the present invention refers to the preparation of (S)-4-fluoromethyl-dihydro-furan-2-one of the formula

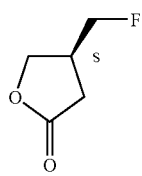

I comprising the steps
a) conversion of a glycidyl ether of the formula

III wherein $R^{1a}$ is a protecting group, with a fluoride salt to provide a fluoro hydrin of formula

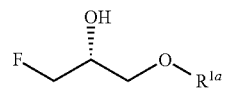

IV wherein $R^{1a}$ is as defined above;
b) esterification of the hydroxy group in the fluoro hydrin of the formula IV with a sulfonic acid derivative;
c) ester substitution with a dialkylmalonate of the formula

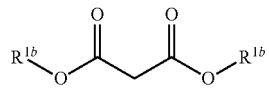

V wherein $R^{1b}$ is lower alkyl or lower phenylalkyl, in the presence of a base to provide an intermediate of the formula

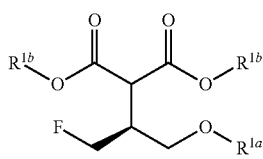

VI wherein $R^{1a}$ and $R^{1b}$ are as defined above, followed by
d) cyclization, hydrolysis and decarboxylation under acidic conditions.

$R^{1a}$ is a hydroxyl protecting group. Preferably, $R^{1a}$ is selected from the group consisting of tert-butyl (t-Bu), allyl, benzyl (Bn), 4-methoxybenzyl (PMB), 3,4-dimethoxybenzyl (DMB) and tetrahydropyran-2-yl (THP).

In a more preferred embodiment $R^{1a}$ has the meaning of t-butyl.

$R^{1b}$ is lower alkyl or lower phenylalkyl. Preferably, $R^{1b}$ is selected from the group consisting of methyl, ethyl, isopropyl, tert-butyl and benzyl. In a more preferred embodiment $R^{1b}$ has the meaning of methyl.

Step a)

Step a) comprises the conversion of a glycidyl ether of formula II with a fluoride salt to provide a fluoro hydrin of formula III.

Preferred glycidyl ether of formula II is the (S)-t-butyl glycidyl ether. The fluoride salt is preferably potassium hydrogen difluoride.

Expediently the reaction is performed in the presence of a phase transfer catalyst. An example for a suitable phase transfer catalyst is tetrabutylammonium hydrogen sulfate which is usually applied in an amount of 0.1 mol % to 10 mol % relating to the glycidyl ether of formula II.

As a rule a glycol such as triethyleneglycol is used as diluent, although different organic solvents may be used.

The reaction temperature is usually selected in the range of 100° C. and 170° C. and more preferably in the range of 130° C. to 140° C. The fluoro hydrin of formula III can be isolated by methods known to the skilled in the art such as by extraction with a suitable organic solvent. Purification may happen by vacuum distillation of the residue. Undesired side products such as the regioisomer (R)-1-tert-butoxy-2-fluoro-propan-1-ol can be separated by careful fractionated vacuum distillation.

Step b)

Step b) comprises the esterification of the hydroxy group in the fluoro hydrin of the formula III with a sulfonic acid derivative.

A suitable sulfonic acid derivative is selected from the group consisting of trifluoromethanesulfonic acid anhydride, trifluoromethanesulfonyl chloride, methanesulfonic acid anhydride, nonafluorobutanesulfonyl fluoride, p-toluene sulfonyl chloride, 2-nitrobenzene sulfonyl chloride and 4-nitrobenzene sulfonyl chloride. Preferred sulfonic acid derivative is trifluoromethanesulfonic acid anhydride.

A suitable amine, such as pyridine, triethylamine or dimethylaminopyridine, is usually present together with an inert organic solvent which may be selected from halogenated hydrocarbons like dichloromethane, chloroform or carbon tetrachloride. Preferably, pyridine and dichloromethane are used. The reaction temperature is selected in the range of –40° C. to 20° C., preferably in the range of –20° C. to 0° C.

The resulting ester can be isolated by methods known to the skilled in the art such as by washing with aqueous hydrochloric acid and subsequent evaporation of the solvent.

Step c)

Step c) comprises ester substitution with a dialkylmalonate of the formula V in the presence of a base to provide the intermediate of the formula VI.

Preferred dialkylmalonate is the dimethylmalonate.

Suitable bases are alkali metal hydrides such as sodium hydride or potassium hydride or alkali metal alkoxides such as sodium tert-butoxide or potassium tert-butoxide. The reaction is as a rule performed in the presence of an organic solvent at a temperature from –20° C. to 50° C., preferably in the range of 0° C. to 20° C. Suitable organic solvents are dimethoxyethane or tetrahydrofurane.

The resulting intermediate of the formula VI can be isolated, but as a rule it is directly converted following the procedure as outlined in step d).

The intermediates of formula

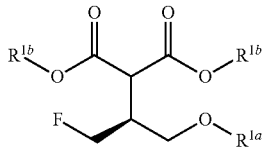

VI wherein $R^{1a}$ is a protecting group and $R^{1b}$ is lower alkyl or lower phenylalkyl, particularly wherein $R^{1a}$ has the meaning of t-butyl and $R^{1b}$ has the meaning of methyl, are novel compounds and thus are further embodiments of the present invention.

Step d)

Step d) comprises the transformation to the target product of formula I which includes an in situ cyclization, hydrolysis and decarboxylation under acidic conditions.

The reaction mixture containing the intermediate of formula VI is acidified with an aqueous mineral acid. Preferably, aqueous sulfuric acid is used. The reaction mixture is as a rule held at a temperature in the range of 70° C. to 110° C. depending on the solvent used for 24 hours to 40 hours. Isolation can happen by methods known to the skilled in the art such as by extraction with a suitable organic solvent, removal of the solvent and subsequent vacuum distillation for purification.

In case $R^{1a}$ or $R^{1b}$ are lower phenylalkyl groups such as benzyl, catalytic hydrogenolysis may also be employed instead of hydrolysis for the deprotection of the hydroxy groups. Typical catalysts used for the hydrogenolysis are Raney Nickel or palladium on charcoal in solvents such as tetrahydrofuran or dimethoxyethane.

The invention further relates to the use of the process as described herein before for the preparation of pyrido[2,1-a] isoquinoline derivatives of the formula

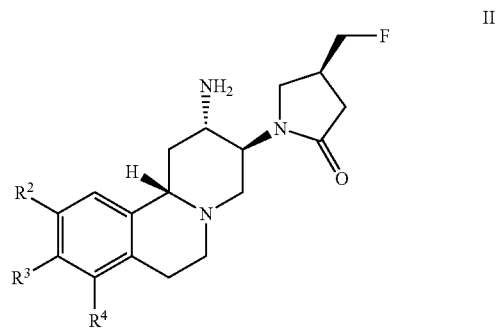

wherein $R^2$, $R^3$ and $R^4$ are each independently selected from the group consisting of hydrogen, halogen, hydroxy, lower alkyl, lower alkoxy or lower alkenyl, wherein lower alkyl, lower alkoxy and lower alkenyl may optionally be substituted by a group selected from lower alkoxycarbonyl, aryl and heterocyclyl;

and of pharmaceutically acceptable salts thereof, according to the following schemes.

Scheme 1

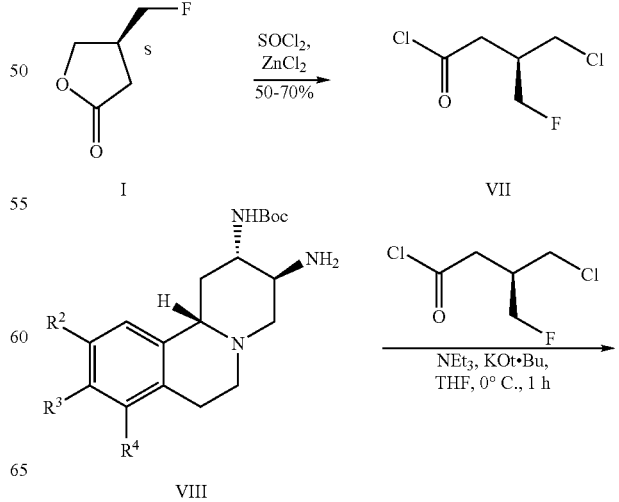

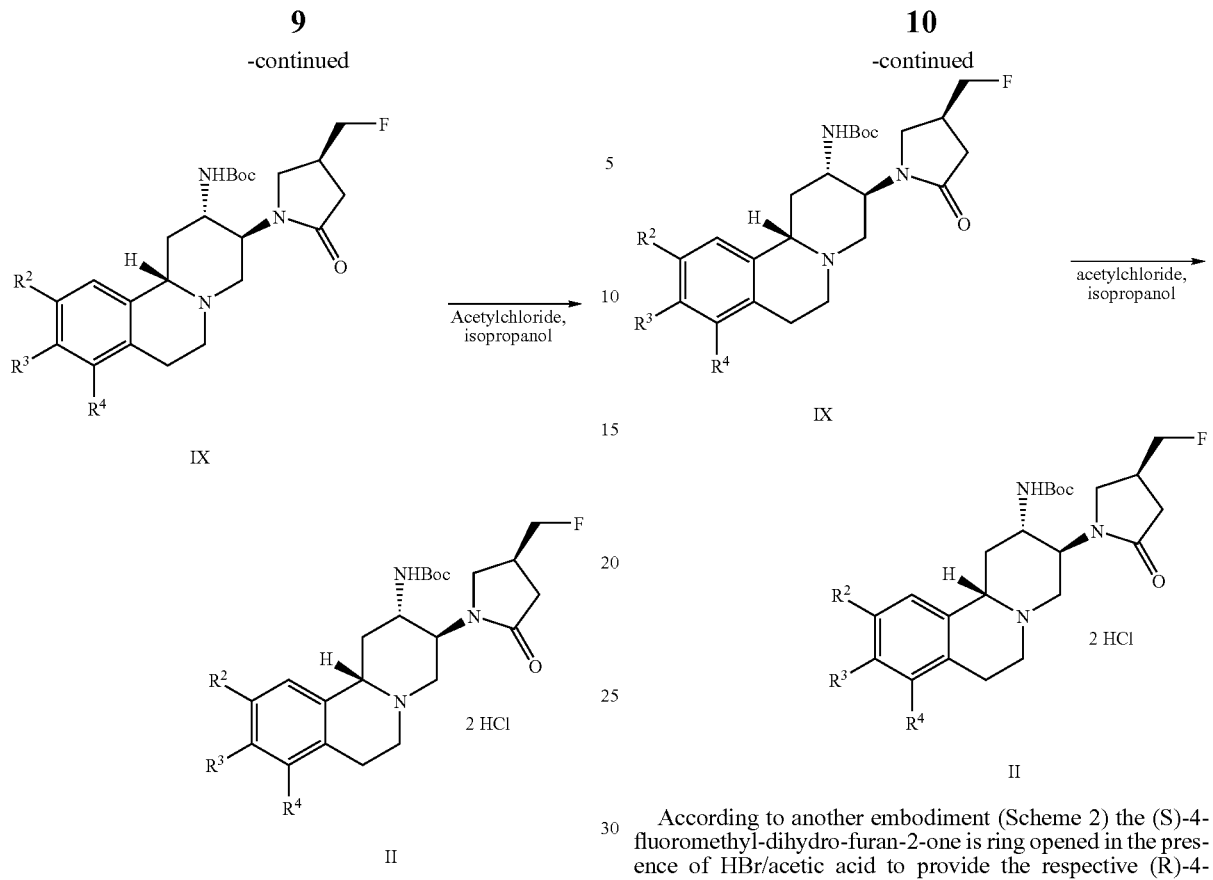

The (S)-4-fluoromethyl-dihydro-furan-2-one can be ring opened in the presence of zinc chloride and thionyl chloride to provide the respective (R)-4-chloro-3-fluoromethyl-butyryl chloride (VII). The acid chloride can then be coupled with the amino-pyrido[2,1-a]isoquinoline derivative (VIII) to form the fluoromethyl-pyrrolidin-2-one derivative of the pyrido[2,1-a]isoquinoline (IX) which after deprotection yields the desired pyrido[2,1-a]isoquinoline derivative (II) (Scheme 1).

According to another embodiment (Scheme 2) the (S)-4-fluoromethyl-dihydro-furan-2-one is ring opened in the presence of HBr/acetic acid to provide the respective (R)-4-bromo-3-fluoromethyl-butyric acid ethyl ester (X). This ester can then be coupled with the amino-pyrido [2,1-a]isoquinoline derivative (VIII) to form the fluoromethyl-pyrrolidin-2-one derivative of the pyrido[2,1-a]isoquinoline (IX) which after deprotection yields the desired pyrido[2,1-a]isoquinoline derivative (II).

Scheme 2

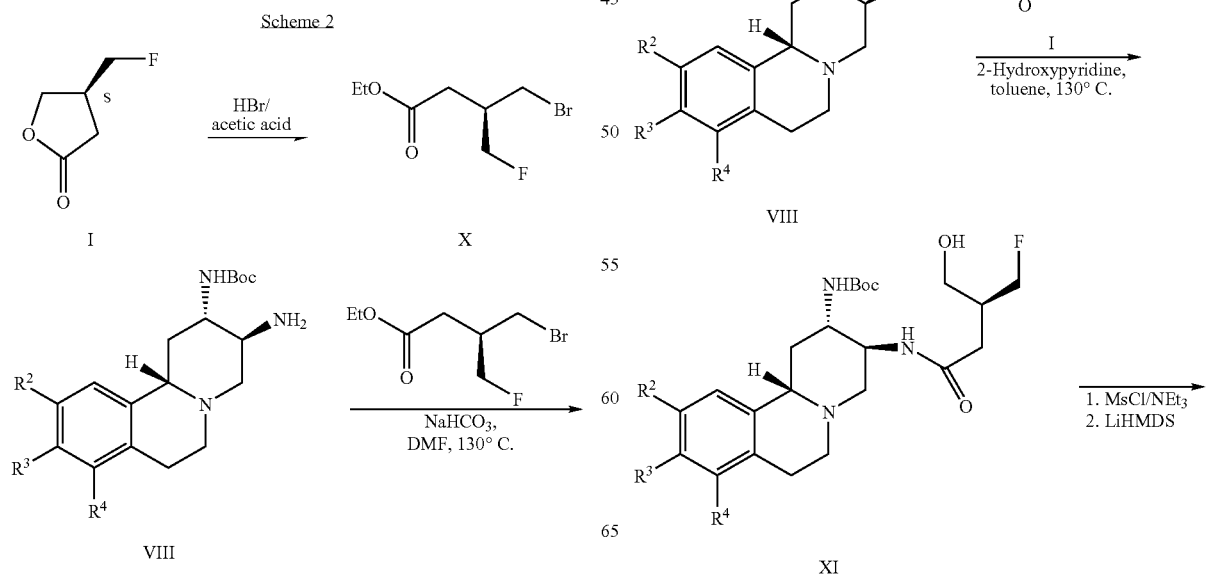

Scheme 3

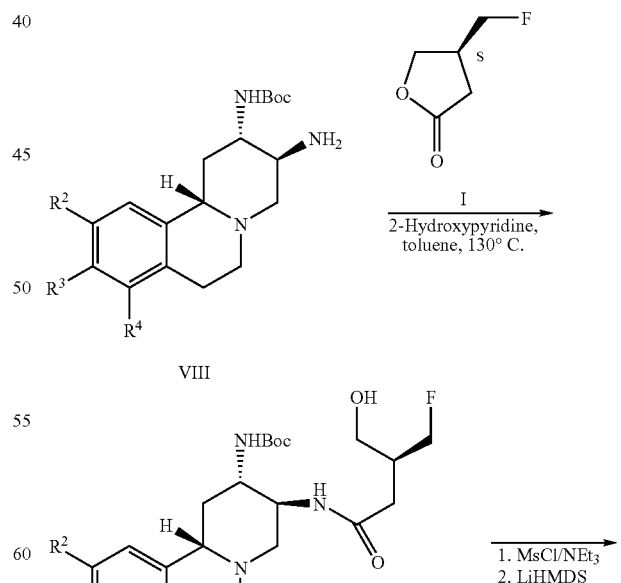

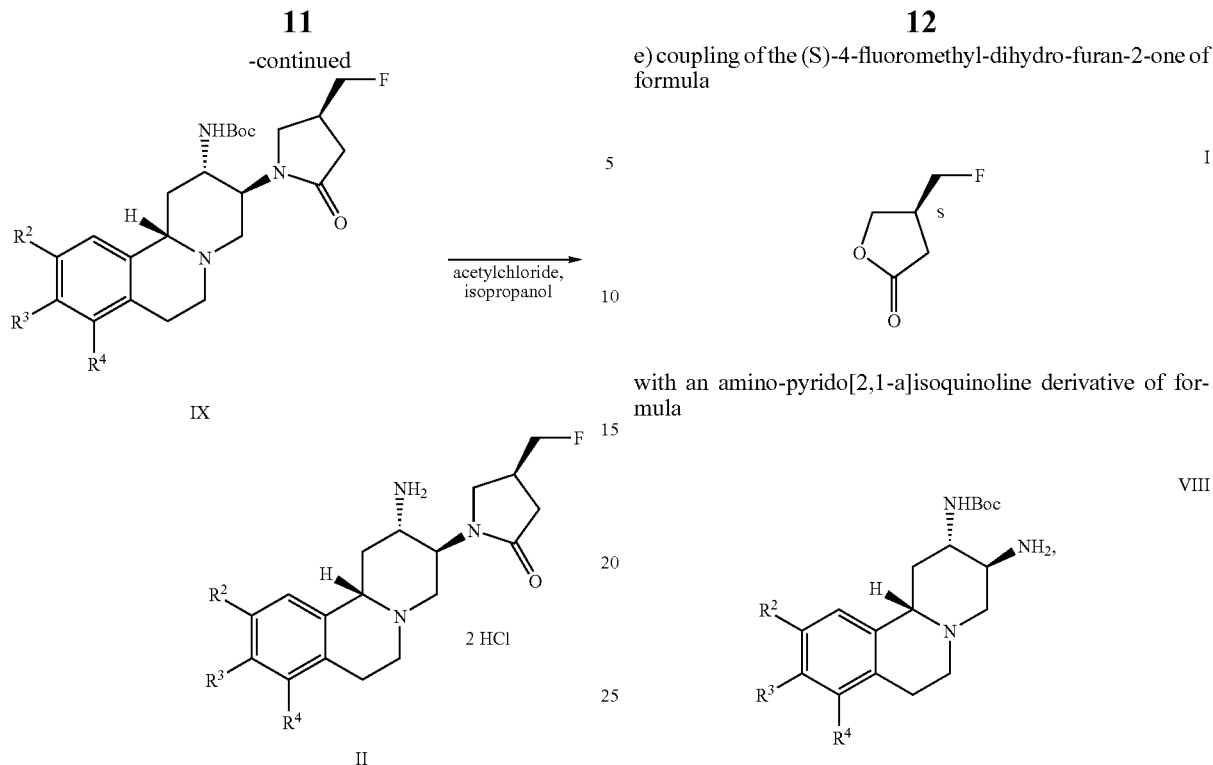

According to still another embodiment (Scheme 3) the (S)-4-fluoromethyl-dihydro-furan-2-one is directly coupled with the amino-pyrido[2,1-a]isoquinoline derivative (VIII) to form the hydroxymethyl derivative of the pyrido[2,1-a]isoquinoline (XI), which is subsequently cyclisized to the fluoromethyl-pyrrolidin-2-one derivative (IX). The latter can be deprotected to yield the desired pyrido[2,1-a]isoquinoline derivative (II).

The invention relates particularly to the use of the process of the present invention for the preparation of (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one.

The invention further relates to a process for the preparation of pyrido[2,1-a]isoquinoline derivatives of the formula wherein R², R³ and R⁴ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl,
which comprises the process of the present invention as defined above followed by e) coupling of the (S)-4-fluoromethyl-dihydro-furan-2-one of formula with an amino-pyrido[2,1-a]isoquinoline derivative of formula wherein R², R³ and R⁴ are as defined above,
f) cyclization of the obtained amide of formula wherein R², R³ and R⁴ are as defined above,
in the presence of a base to obtain a compound of formula wherein R², R³ and R⁴ are as defined above and
g) deprotection of the amino group.

The invention further relates particularly to a process for the preparation of (S)-1-((2S,3S,11bS)-2-amino-9,10- dimethoxy-1,3,4,6,7,11b-hexahydro-2H-pyrido[2,1-a]isoquinolin-3-yl)-4-fluoromethyl-pyrrolidin-2-one, which comprises the process of the present invention as defined above followed by e) coupling of the (S)-4-fluoromethyl-dihydro-furan-2-one of formula

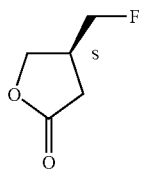

I with (2S,3S,11bS)-3-amino-9,10-dimethoxy-1,3,4,6,7,11b-hexahydro-2H-pyrido[2,1-a]isoquinolin-2-yl)-carbamic acid tert-butyl ester, f) cyclization of the obtained (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester in the presence of a base, and g) deprotecting the obtained (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester.

The pyrido[2,1-a]isoquinoline derivatives of formula (II) as disclosed in the PCT Int. Application WO 2005/000848 are useful for the treatment and/or prophylaxis of diseases which are associated with DPP IV such as diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of obesity, inflammatory bowel disease, Colitis Ulcerosa, Morbus Crohn, and/or metabolic syndrome or □-cell protection. Furthermore, the compounds of the present invention can be used as diuretic agents and for the treatment and/or prophylaxis of hypertension. Unexpectedly, the compounds of the present invention exhibit improved therapeutic and pharmacological properties compared to other DPP-IV inhibitors known in the art, such as e.g. in context with pharmacokinetics and bioavailability.

The following examples shall illustrate the invention without limiting it.

EXAMPLES

Example 1

Preparation of (S)-tert-butyl glycidyl ether (S)-1

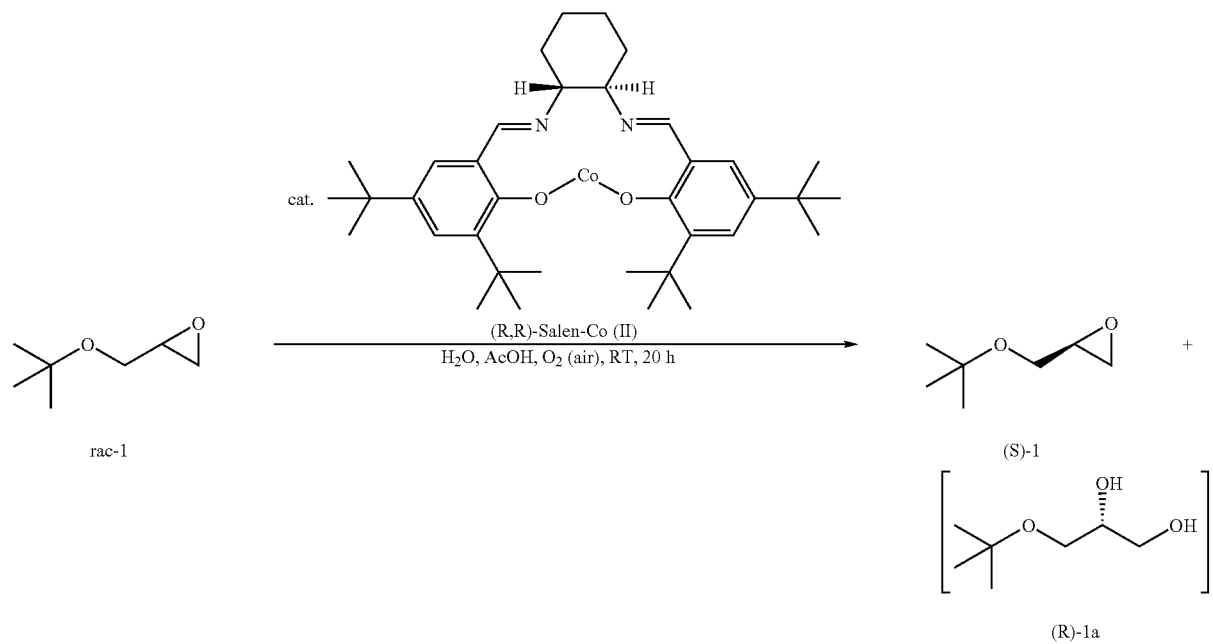

In a 500 ml round bottomed flask equipped with thermometer and a magnetic stirrer and an ice bath 6.04 g (1R,2R)-(−)-1,2-cyclohexanediamino-N,N'-bis-(3,5-di-t-butylsalicylidene) cobalt (II) (10 mmol; Strem Chemicals) and 260.38 g rac tert-butyl glycidyl ether (2000 mmol) and 2.40 g acetic acid (40 mmol) and 20 ml THF (tetrahydrofurane) were cooled under stirring to 0° C. and 19.82 g deionized water (1100 mmol) were added all at once. The dark red reaction mixture was stirred under an air atmosphere for 0.5 h at 0° C. and for 23 h at RT. Vacuum distillation over a column filled with "Fenske" glass rings (20×2 cm column; "Fenske" glass rings Ø≅4 mm) afforded 113.2 g (43.5%) (S)-tert-butyl glycidyl ether (S)-1 as colorless liquid, b.p. 84-86° C./100 mbar.

Example 2

Preparation of (R)-1-tert-butoxy-3-fluoro-propan-2-ol (R-2)

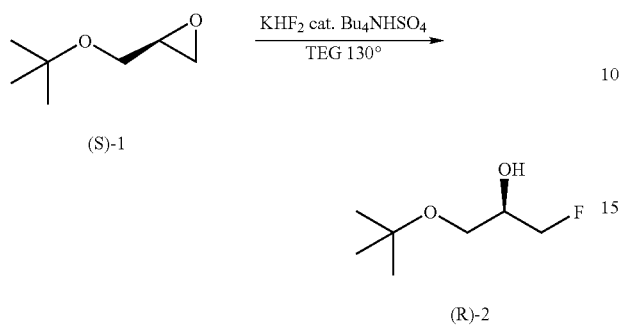

In a 750 ml four-necked flask equipped with a condenser, a thermometer, a mechanical stirrer, a device for supplying an inert atmosphere (Ar) and an oil bath a white suspension of 104.2 g (S)-tert-butyl glycidyl ether (S)-2 (800 mmol from example 1), 80 ml triethylene glycol, 125.0 g potassium hydrogen difluoride (1600 mmol) and 1.36 g tetrabutylammonium hydrogen sulfate (4.0 mmol; Fluka) were stirred at 130° C. for 20 h. After cooling to RT (room temperature), the brown suspension was diluted with 160 ml dichloromethane and washed with 500 ml deionized water, 160 ml aqueous 5% NaHCO₃ and 160 ml 10% brine. All aqueous layers were extracted sequentially with 80 ml dichloromethane and the combined organic layers were dried over K₂CO₃ and filtered. After removal of the main part of the solvent by distillation at normal pressure the residue (~200 ml) was vacuum distilled over a column (20×2 cm) filled with "Fenske" glass rings affording 76.1 g (R)-fluorohydrin (R)-2 (63.3% as a colorless liquid (bp. 104-105° C./100 mbar).

Example 3

Preparation of trifluoromethanesulfonic acid (R)-1-tert-butoxymethyl-2-fluoror-ethyl ester (R)-3

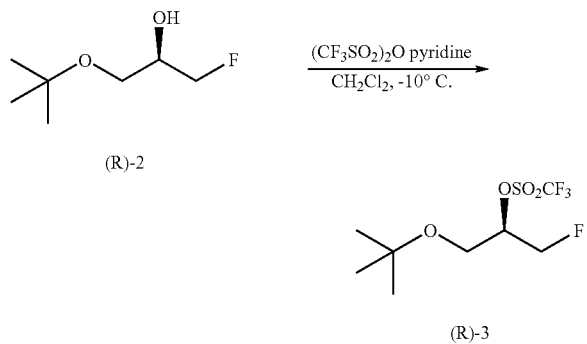

In a 750 ml four-necked flask equipped with a condenser, a thermometer, a mechanical stirrer, a device for supplying an inert atmosphere (Ar) and an ice-methanol bath 32.2 ml pyridine (400 mmol) were added all at once to a colorless solution of 30.04 g (R)-fluorohydrin (R)-2 (200 mmol; example 2) in 300 ml dichloromethane at −10° C. 34.7 ml trifluoromethanesulfonic anhydride (210 mmol) was added at −10° C. over 1 hand stirring was continued at −10° C. for 1 h. brine and 120 ml 10% Na₂CO₃. All aqueous layers were extracted sequentially with 80 ml dichloromethane and the combined organic layers were dried over K₂CO₃. After filtration the solvent was removed by rotary evaporation (20° C./≧10 mbar) affording 55.5 g crude triflate (R)-3 as yellow oil which was stored at −20° C.

Example 4a

Preparation of (S)-4-fluoromethyl-dihydro-furan-2-one (S)-4 (with NaOtBu)

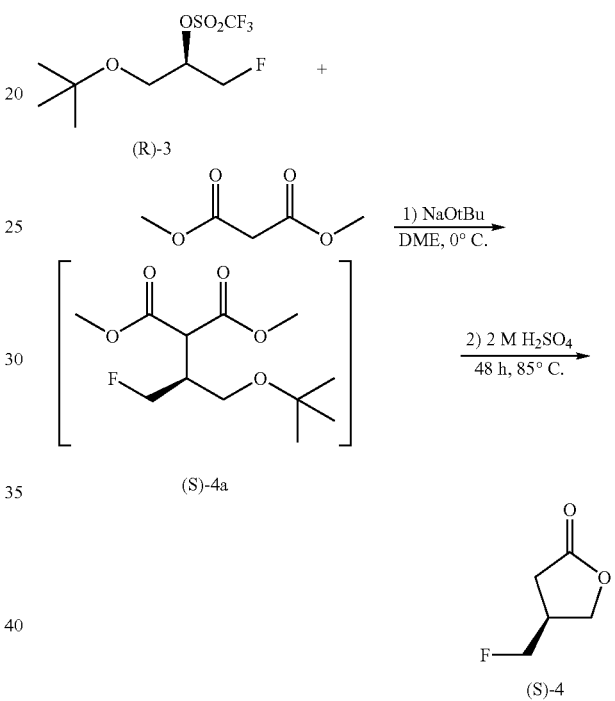

Substitution:

In a 750 ml four-necked flask equipped with a mechanical stirrer, a condenser, a dropping funnel, a thermometer, a device for supplying an inert atmosphere (Argon) and ice-methanol or oil bath 21.14 g sodium tert-butoxide (220 mmol) were dissolved in 200 ml 1,2-dimethoxyethane at 20° C. and 31.71 g dimethylmalonate (240 mmol) were added at 20° C. over 15 min. After cooling to 0° C. 55.5 g triflate (R)-4 (≦200 mmol; from example 3) were added at 0° C. over 15 min and the orange reaction mixture was stirred at 0° C. for 7 h.

The intermediate (S)-4a was identified via ¹H-NMR (CDCl₃): δ 1.15 (s, 9H, C(CH₃)₃), 2.58-2.78 (m, 1H, CH), 3.47 (m, 2H, CH₂O), 3.67 (d, 1H, CH), 3.74 and 3.75 (s, each 3H, CO₂CH₃), 4.52 and 4.67 (m, each 1H, CH₂F.

Cyclization, Hydrolysis & Decarboxylation:

The ice-methanol bath was removed. 200 ml 2M H₂SO₄ (400 mmol) were added all at once and the yellow reaction mixture was heated under reflux for 48 h. After cooling to RT the reaction mixture was extracted three times with 200 ml dichloromethane and all three organic layers were washed with 100 ml 2% NaHCO₃. The combined organic layers were dried (Na₂SO₄), filtered and the solvent was removed by rotary evaporation (30-45° C./≧10 mbar) affording 22.1 g crude, brown oil. Vacuum distillation gave 19.8 g (84%) fluoromethyl-butyrolactone (S)-4 as colorless oil, b.p. 68-69° C./0.5 mbar.

Example 4b

Preparation of (S)-4-fluoromethyl-dihydro-furan-2-one (S)-4 (with NaH)

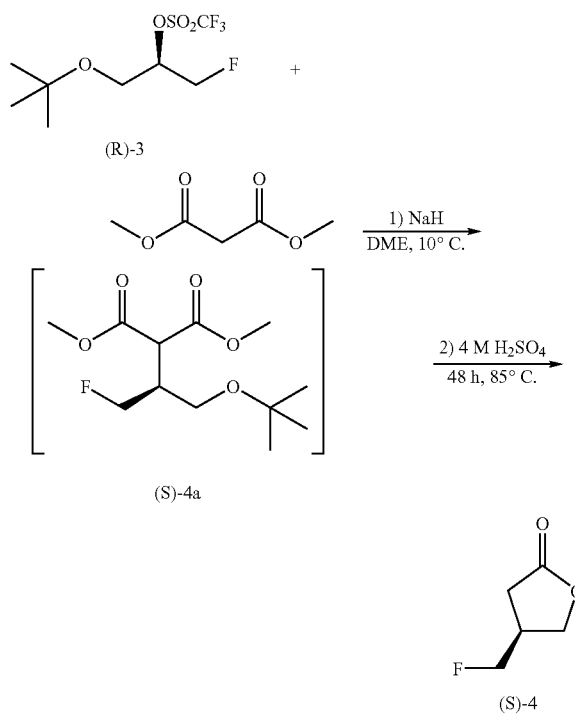

Substitution:

In a 750 ml four-necked flask equipped with a mechanical stirrer, a condenser, a dropping funnel, a thermometer, a device for supplying an inert atmosphere (Ar) and ice-methanol or oil bath to a suspension of 9.6 g sodium hydride 60% (240 mmol) in 200 ml 1,2-dimethoxyethane were added 33.0 g dimethyl malonate (250 mmol) at 20° C. over 15 min. Stirring at RT was continued for 1 h. The colorless, turbid solution was cooled to 0° C., 55.5 g triflate (R)-3 (<200 mmol; from example 3) were added at 0° C. over 15 min and the orange reaction mixture was stirred at 10° C. for 5 h.

Cyclization, Hydrolysis & Decarboxylation:

200 ml 4M $H_2SO_4$ (800 mmol) were added all at once and the yellow reaction mixture was heated under reflux for 40 h (~85° C.). After cooling to RT, the reaction mixture was transferred into a separatory funnel and diluted with 200 ml deionized water. After removal of the small upper oily layer (mineral oil from the sodium hydride) the product was extracted three times with 400 ml dichloromethane. All organic layers were washed sequentially twice with 100 ml 10% brine and the combined organic layers were dried ($Na_2SO_4$). The solvent was removed by rotary evaporation (30-45° C./≧10 mbar) affording 22.1 g crude, orange oil. Vacuum distillation gave 19.4 g (82%) fluoromethyl-lactone (S)-1 as a light yellow oil, b.p. 65-68° C./0.5 mbar.

Example 5

Preparation of (R)-4-chloro-3-fluoromethyl-butyryl chloride

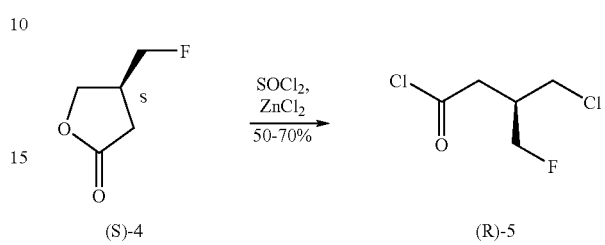

A 350 ml reactor equipped with a mechanical stirrer, a Pt-100 thermometer and an argon inlet was charged with 226 g (1.90 mol) (S)-4-fluoromethyl-dihydro-furan-2-one, 64.9 g (476 mmol) zinc chloride and 698 ml (9.52 mol) thionyl chloride. The mixture was refluxed for 66 h, then allowed to cool to RT. The white precipitate, which already formed during the reaction, was filtered off under an argon atmosphere and washed with a small amount of thionyl chloride. The filtrate was distilled as follows: Thionyl chloride was collected as a first fraction at 30° C. oil bath temperature/20 mbar. Then the oil bath temperature was slowly increased and the fractions between 57 and 62° C./1 mbar were collected, to give 196 g (R)-4-chloro-3-fluoromethyl-butyryl chloride (58% yield; assay: 97%).

Example 6

Preparation of (2S,3S,11bS)-3-((4S)-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester

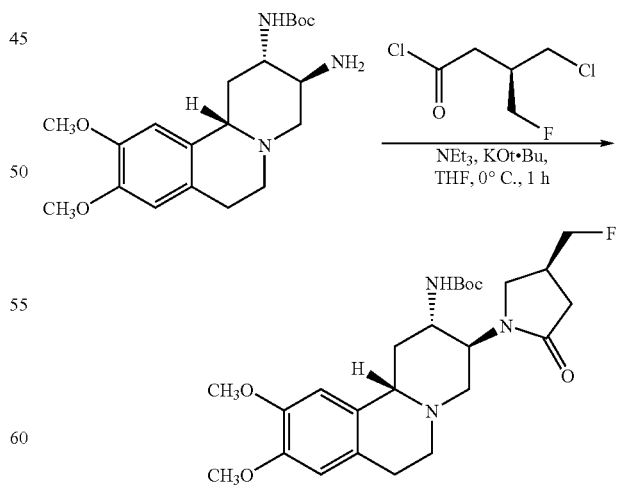

a nitrogen inlet was charged with 160 g (419 mmol) (2S, 3S,11bS)-3-(3-amino-9,10-dimethoxy-1,3,4,6,7,11b-hexahydro-2H-pyrido[2,1-a]isoquinolin-2-yl)-carbamic acid tert-butyl ester, 1.50 L dry THF and 29.3 ml (209 mmol)

triethylamine. The suspension was cooled to 0-5° C. and a solution of 97.4 g (544 mmol) (R)-4-chloro-3-fluoromethyl-butyryl chloride in 417 ml dry THF was added during 90 min, maintaining the temperature at 0-5° C. After the addition of about half of the acid chloride solution, the reaction mixture became thick, but still remained stirrable. The mixture was stirred for 1.5 h at 0-5° C., another portion of 9.37 g (52.7 mmol) acid chloride in 35 ml dry THF was added and the mixture was stirred for another 30 min at 0-5° C. A suspension of 145 g (1.26 mol) potassium tert.-butylate in 900 ml dry THF was added during 35 min, maintaining the temperature at below 6° C. After completed addition the mixture was stirred overnight at 0° C., poured on 6.2 L half saturated brine and extracted with 6.2 L ethyl acetate. The organic layer was washed with 3.2 L half saturated brine, and the combined aqueous phases were extracted twice with 2.2 L ethyl acetate. The combined organic layers were filtered over a pad of 800 g sodium sulfate, concentrated on a rotatory evaporator at 45° C./10 mbar and dried at 40° C./0.1 mbar for 16 h, to give 225 g crude product. This material was chromatographed over silica gel with dichloromethane/THF 3:1 as eluent, to give 168 g product. This material was suspended in 800 ml methanol, heated to reflux and after 15 min allowed to slowly reach RT, resulting in a thick, but well stirrable suspension. After 4 h at RT, the reddish brown mixture was stirred at 0° C. overnight, followed by −15 to −20° C. during 2 h. The crystals were filtered off, washed portionwise with totally 250 ml cold TBME (pre-cooled to −15° C.) and dried for 6 h at 45° C./9 mbar, followed by 15 h at 45° C./0.1 mbar, to give 127 g lactam (64% yield; assay: 100%)

Example 7

Preparation of (2S,3S,11bS)-3-(3-Fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester

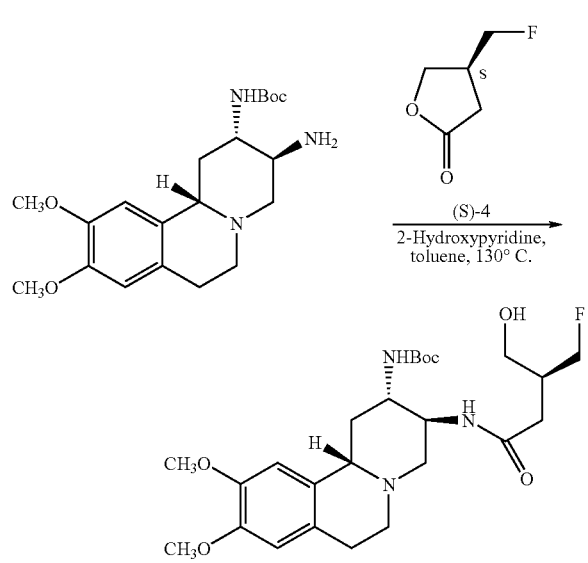

A 1.5 L reactor equipped with a mechanical stirrer, a Pt-100 thermometer, a dropping funnel and a nitrogen inlet was charged with 50 g (128 mmol) (2S,3S,11bS)-3-amino-9,10-dimethoxy-1,3,4,6,7,11b-hexahydro-2H-pyrido[2,1-a]isoquinolin-2-yl)-carbamic acid tert-butyl ester, 500 ml toluene and 2.51 g (25.6 mmol) 2-hydroxypyridine. To this slightly brownish suspension, 22.7 g (192 mmol) of (S)-4-fluoromethyl-dihydro-furan-2-one was added dropwise at RT. No exothermy was observed during the addition. The dropping funnel was rinsed portionwise with totally 100 ml toluene. The suspension was heated to reflux, whereas it turned into a clear solution starting from 60° C., after 40 min under reflux a suspension formed again. After totally 23 h under reflux, the thick suspension was cooled to RT, diluted with 100 ml dichloromethane and stirred for 30 min at RT. After filtration, the filter cake was washed portion wise with totally 200 ml toluene, then portion wise with totally 100 ml dichloromethane. The filter cake was dried at 50° C./10 mbar for 20 h, to give 60.0 g product (94% yield; assay: 100%).

Example 8

Preparation of (2S,3S,11bS)-3-((4S)-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester

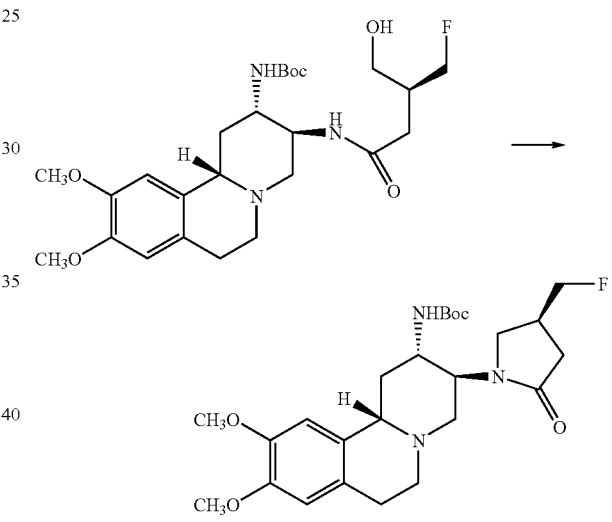

A 1.5 L reactor equipped with a mechanical stirrer, a Pt-100 thermometer, a dropping funnel, a cooling bath and a nitrogen inlet was charged with 28 g (56.5 mmol) of (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester and 750 ml THF. The mixture was cooled to 0° C. and a solution of 6.17 ml (79 mmol) methanesulfonic acid in 42 ml THF was added during 10 min, maintaining the temperature at 0-5° C. At 0° C. a solution of 12.6 ml (90.2 mmol) triethylamine in 42 ml THF was added during 15 min. The resulting suspension was stirred for 80 min at 0-5° C., whereas it became gradually thicker. Then 141 ml (141 mmol) 1 M lithium-bis(trimethyl-silyl)amide were added to the mixture during 15 min, whereas the suspension dissolved. The solution was allowed to reach RT during 60 min under stirring. 500 ml water was added without cooling, the mixture was extracted and the aqueous phase was subsequently extracted with 500 ml and 250 ml dichloromethane. The organic layers were each washed with 300 ml half saturated brine, combined and evaporated on a rotatory evaporator. The resulting foam was dissolved in 155 ml dichloromethane, filtered and again evaporated to give 30.5 g crude product as a slightly brownish foam. This material was dissolved in 122 ml methanol, resulting in a thick suspension, which dissolved on heating to reflux. After 20 min of reflux the solution was allowed to gradually cool to RT during 2 h, whereas crystallization started after 10 min. After 2 h the suspension was cooled to 0° C. for 1 h, followed by −25° C. for 1 h. The crystals were filtered off via a pre-cooled glass sinter funnel, washed portionwise with 78 ml TBME and dried for 18 h at 45° C./20 mbar, to give 21.0 g product as white crystals (77% yield; assay: 99.5%).

Example 9

Preparation of (2S,3S,11bS)-1-(2-amino-9,10-dimethoxy-1,3,4,6,7,11b-hexahydro-2H-pyrido[2,1-a]isoquinolin-3-yl)-4(S)-fluoromethyl-pyrrolidin-2-one dihydrochloride

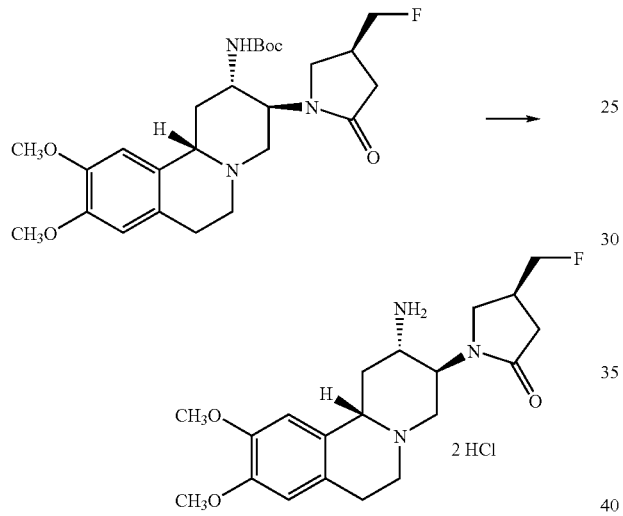

a nitrogen inlet was charged with 619 g (1.30 mol) of (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester, 4.2 L isopropanol and 62 ml water and the suspension was heated to 40-45° C. In a second vessel, 1.98 L isopropanol was cooled to 0° C. and 461 ml (6.50 mol) acetyl chloride was added during 35 min, maintaining the temperature at 0-7° C. After completed addition, the mixture was allowed to reach ca. 15° C. and was then slowly added to the first vessel during 1.5 h. After completed addition the mixture was stirred for 18 h at 40-45° C., whereas crystallization started after 1 h. The white suspension was cooled to 20° C. during 2 h, stirred at that temperature for 1.5 h and filtered. The crystals were washed portionwise with 1.1 L isopropanol and dried for 72 h at 45° C./20 mbar, to give 583 g of the product as white crystals (100% yield; assay: 99.0%)

It is to be understood that the invention is not limited to the particular embodiments of the invention described above, as variations of the particular embodiments may be made and still fall within the scope of the appended claims.

What is claimed is:

1. A process for the preparation of (S)-4-fluoromethyl-dihydro-furan-2-one of the formula

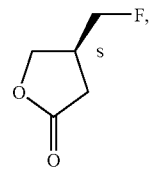

comprising the steps:
a) conversion of a glycidyl ether of the formula

wherein $R^{1a}$ is a protecting group, with a fluoride salt to provide a fluoro hydrin of formula

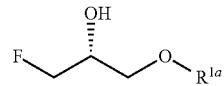

wherein $R^{1a}$ is as defined above;
b) esterification of the hydroxy group in the fluoro hydrin of the formula IV with a sulfonic acid derivative;
c) ester substitution with a dialkylmalonate of the formula

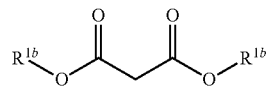

wherein $R^{1b}$ is lower alkyl or lower phenylalkyl, in the presence of a base to provide an intermediate of the formula

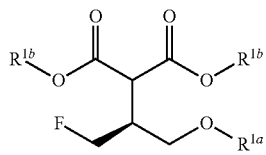

wherein $R^{1a}$ and $R^{1b}$ are as defined above, followed by
d) cyclization, hydrolysis and decarboxylation under acidic conditions.

2. The process according to claim 1, characterized in that $R^{1a}$ is tert-butyl.

3. The process according to claim 1, characterized in that $R^{1b}$ is methyl.

4. The process according to claim 1, characterized in that the fluoride salt used for the conversion in step a) is potassium hydrogen difluoride.

5. The process according to claim 1, characterized in that the conversion in step a) is performed in the presence of a phase transfer catalyst.

6. The process according to claim 5, characterized in that the phase transfer catalyst is tetrabutylammonium hydrogen sulfate.

7. The process according to claim 1, characterized in that the conversion in step a) is performed in the presence of triethyleneglycol.

8. The process according to claim 1, characterized in that the sulfonic acid derivative used for the esterification in step b) is selected from trifluoromethanesulfonic acid anhydride, trifluoromethanesulfonyl chloride, methanesulfonic acid anhydride, nonafluorobutane-sulfonyl fluoride, p-toluene sulfonyl chloride, 2-nitrobenzene sulfonyl chloride and 4-nitrobenzene sulfonyl chloride.

9. The process according to claim 1, characterized in that the esterification in step b) is performed with trifluoromethanesulfonic acid anhydride in the presence of an amine and an inert organic solvent at a temperature in the range of −40° C. to 20° C.

10. The process according to claim 1, characterized in that the base used for the ester substitution in step c) is selected from an alkali metal hydride or an alkali metal alkoxide.

11. The process according to claim 10, characterized in that sodium tert-butoxide is used.

12. The process according to claim 1, characterized in that the ester substitution in step c) is performed in the presence of an organic solvent at a temperature range from −20° C. to 50° C.

13. The process according to claim 1, characterized in that the acid used for the transformation in step d) is an aqueous mineral acid.

14. The according to claim 13, characterized in that aqueous sulfuric acid is used.

15. A process for the preparation of pyrido[2,1-a]isoquinoline derivatives of the formula

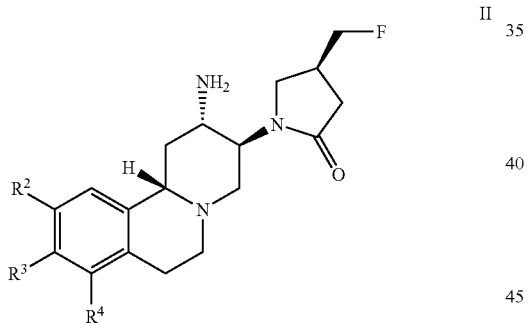

II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, comprising the process according to claim 1 followed by e) coupling of the (S)-4-fluoromethyl-dihydro-furan-2-one of formula

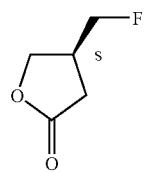

I with an amino-pyrido[2,1-a]isoquinoline derivative of formula

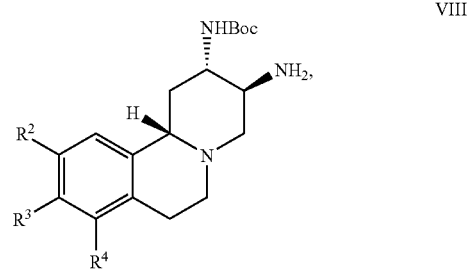

VIII wherein $R^2$, $R^3$ and $R^4$ are as defined above, f) cyclization of the obtained amide of formula

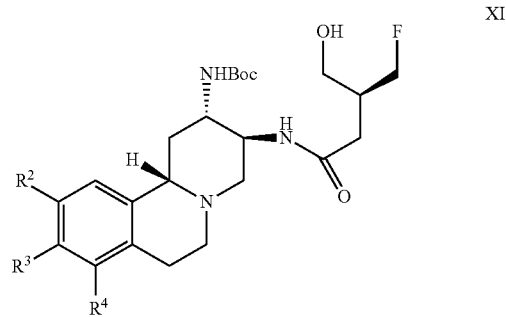

XI wherein $R^2$, $R^3$ and $R^4$ are as defined above, in the presence of a base to obtain a compound of formula

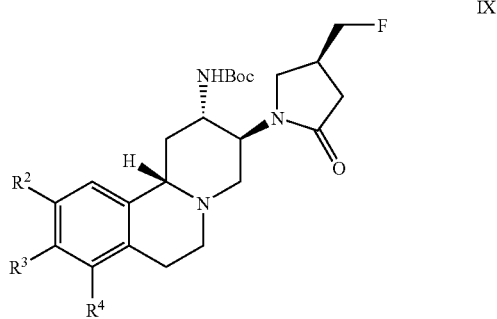

IX wherein $R^2$, $R^3$ and $R^4$ are as defined above and g) deprotection of the amino group.

16. The process according to claim 15 for the preparation of (S)-1-((2S,3S,11bS)-2-amino-9,10-dimethoxy-1,3,4,6,7,11b-hexahydro-2H-pyrido[2,1-a] isoquinolin-3-yl)-4-fluoromethyl-pyrrolidin-2-one, comprising the process according to claim 1 followed by e) coupling of the (S)-4-fluoromethyl-dihydro-furan-2-one of formula

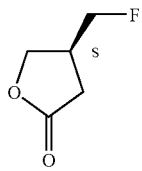

with (2S,3S,11bS)-3-amino-9,10-dimethoxy-1,3,4,6,7,11b-hexahydro-2H-pyrido[2,1-a]isoquinolin-2-yl)-carbamic acid tert-butyl ester, f) cyclization of the obtained (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester in the presence of a base, and g) deprotecting the obtained (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester.

\* \* \* \* \*